United States Patent [19]

Sandridge

[11] Patent Number: 5,368,579
[45] Date of Patent: Nov. 29, 1994

[54] PERFUSION CONTROLLED GUIDING CATHETER APPARATUS AND METHOD

[76] Inventor: James B. Sandridge, 2044 Eagle Nest, Lewisville, Tex. 75067

[21] Appl. No.: 919,049

[22] Filed: Jul. 23, 1992

[51] Int. Cl.⁵ ............................................. A61M 5/00
[52] U.S. Cl. ..................... 604/249; 604/53; 604/256
[58] Field of Search ............. 604/53, 246, 247, 249, 604/256, 264, 280, 281; 128/658

[56] References Cited

U.S. PATENT DOCUMENTS

| | | | |
|---|---|---|---|
| 2,220,493 | 11/1940 | Pixler | 210/239 |
| 4,137,906 | 2/1979 | Akiyama et al. | 128/325 |
| 4,301,797 | 11/1981 | Pollack | 604/256 |
| 4,643,712 | 2/1987 | Kulik et al. | 604/249 |
| 4,705,507 | 11/1987 | Boyles . | |
| 4,723,946 | 2/1988 | Kay | 604/249 |
| 4,787,882 | 11/1988 | Claren | 604/264 |
| 4,857,054 | 8/1989 | Helfer . | |
| 4,968,306 | 11/1990 | Huss et al. | 604/264 |
| 4,981,471 | 1/1991 | Quinn et al. . | |
| 5,163,921 | 11/1992 | Feiring | 604/247 |
| 5,180,364 | 1/1993 | Ginsburg | 604/247 |

FOREIGN PATENT DOCUMENTS

| | | | |
|---|---|---|---|
| 2340078 | 9/1977 | France | 604/256 |
| 2003038 | 3/1979 | United Kingdom | 604/256 |

Primary Examiner—John D. Yasko
Assistant Examiner—Anthony Gutowski
Attorney, Agent, or Firm—Harris, Tucker & Hardin

[57] ABSTRACT

A guiding catheter used for coronary angioplasty procedures includes an plurality of ports in the wall of the guiding catheter. A moveable member is disposed in the lumen or wall of the guiding catheter and is selectively movable between a first position blocking the ports and a second position not blocking the ports. The moveable member is shown as an elongated stylet, a hollow tube with matching ports or a plurality of inflatable balloons. The catheter is positioned adjacent to an artery to be examined. The ports are blocked by the moveable member while contrast medium is injected through the guide catheter to the artery. The ports are opened otherwise to enable the flow of blood between the catheter and the artery.

14 Claims, 3 Drawing Sheets

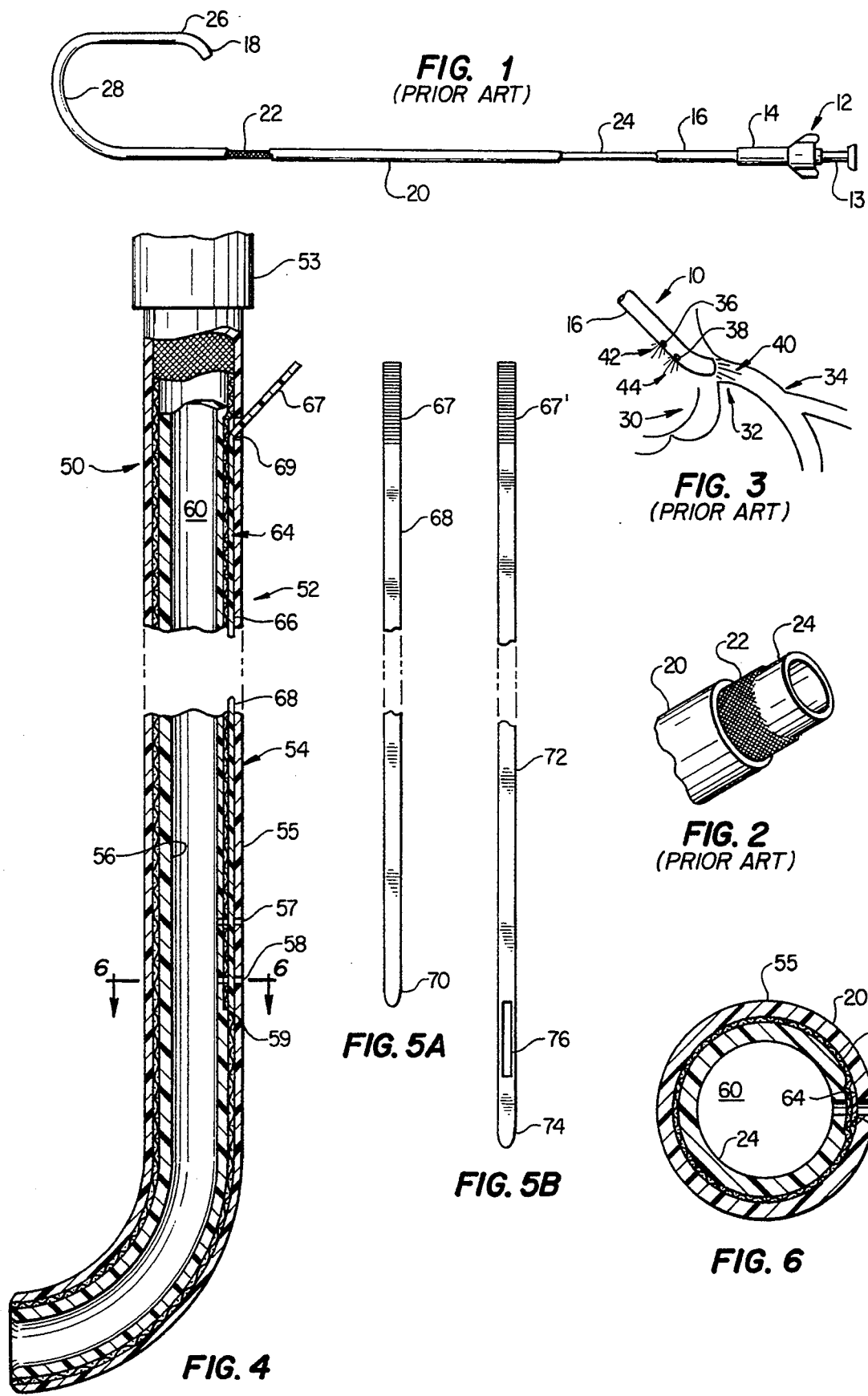

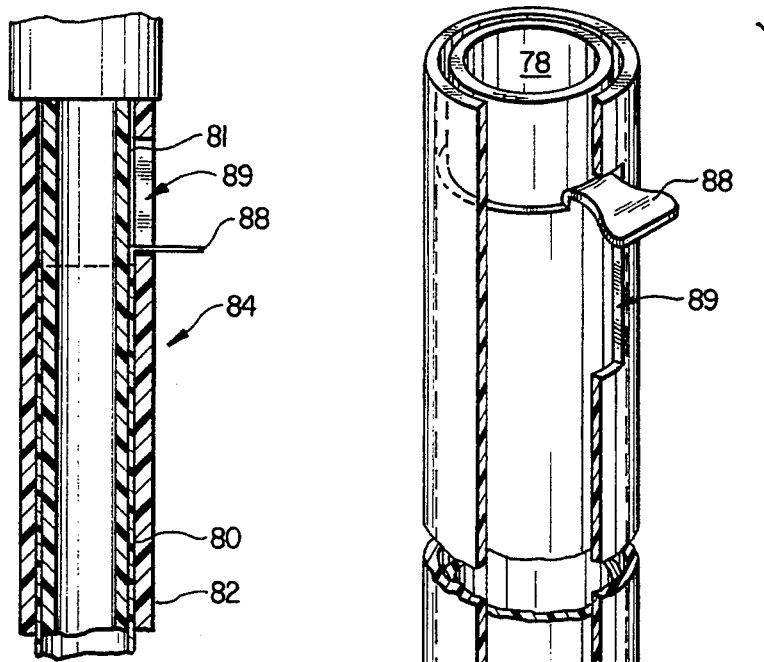
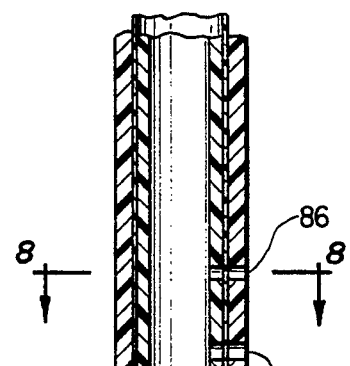
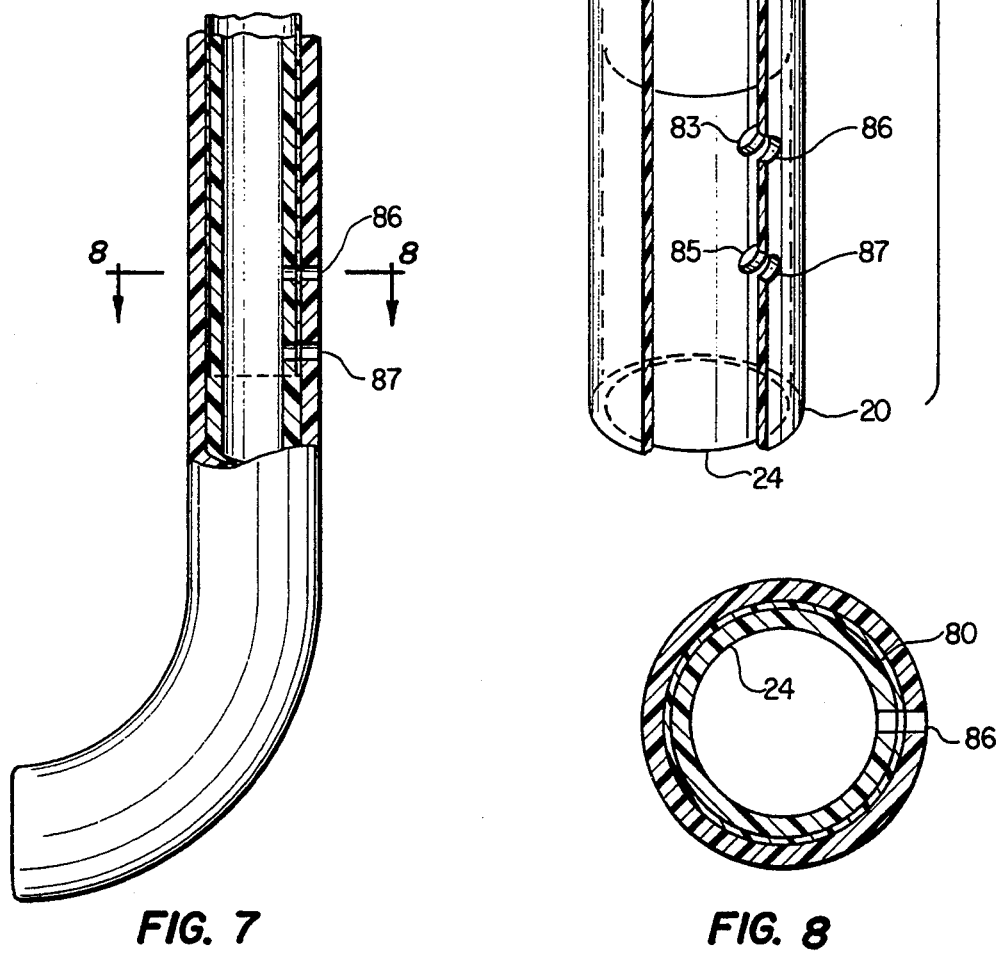
FIG. 7   FIG. 8

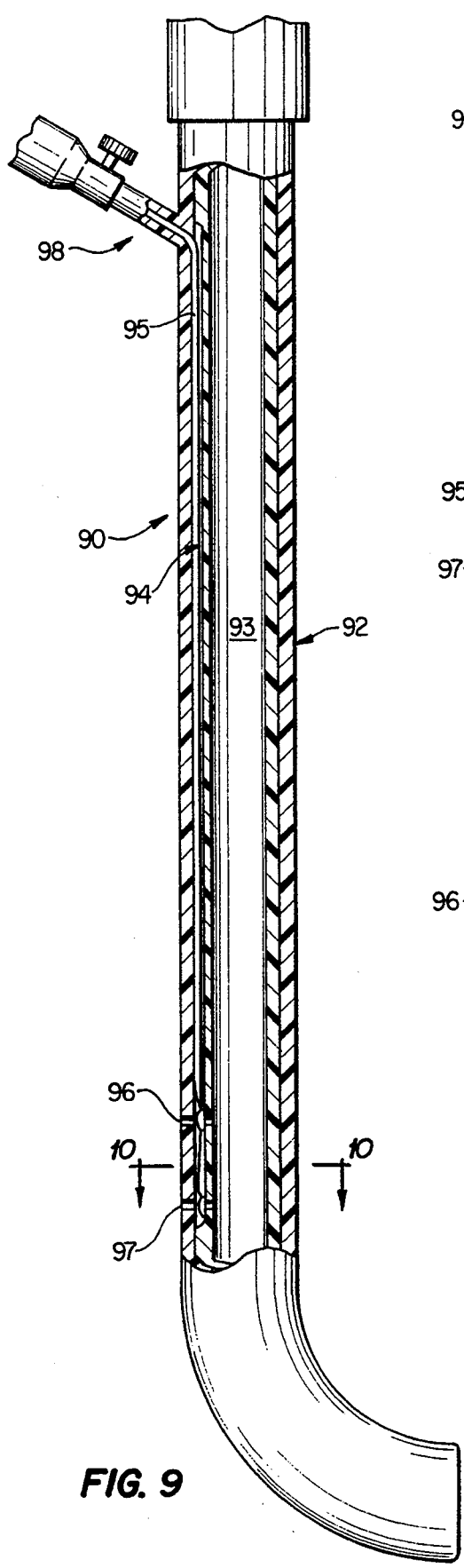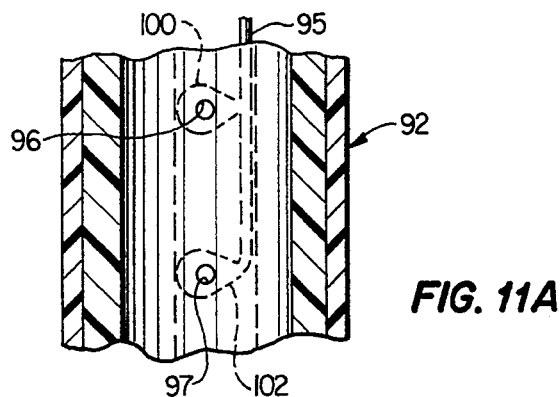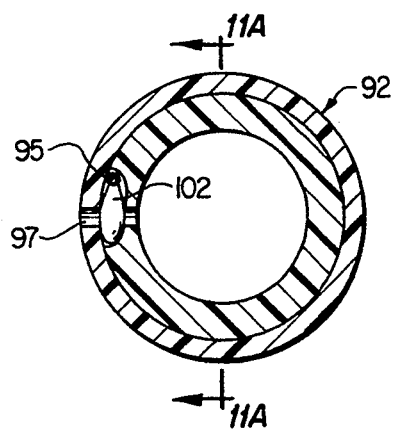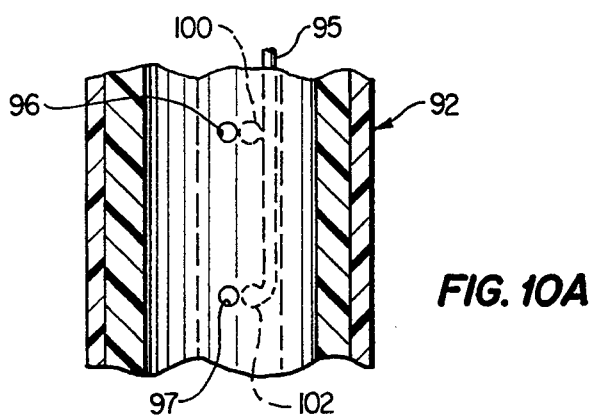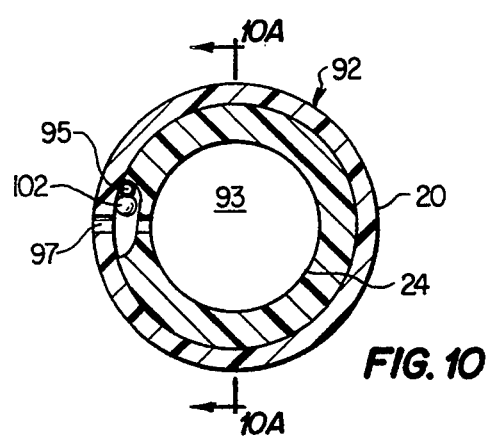

PERFUSION CONTROLLED GUIDING CATHETER APPARATUS AND METHOD

BACKGROUND OF THE INVENTION

The present invention relates to a guiding catheter used in Percutaneous Transluminal Coronary Angioplasty procedures. More particularly the present invention concerns a guiding catheter having perfusion ports which are alternately covered to control the direction of flow of injected contrast medium and opened to enable the flow of the artery being treated.

In Percutaneous Transluminal Coronary Angioplasty (PTCA) procedures, a balloon catheter is introduced into an artery for the purposes of enlarging a vessel or opening a clogged artery or stuck valve in the heart or elsewhere to restore normal blood flow. A peripheral introduction of a balloon tip catheter enlarges and dilates a narrowed arterial lumen by inflating the catheter tip.

The PTCA procedure is begun by the introduction of a guiding catheter through an artery in the groin or arm. The guiding catheter is advanced to where the coronary arteries branch off the heart. Then x-ray dye medium is inserted through the guiding catheter into the coronary artery to look for blockages using an x-ray monitor. Once a blockage is found, a guide wire and then a balloon catheter is inserted to the blockage area where inflation of the balloon opens the artery to restore normal blood flow.

During PTCA, a guiding catheter may block the ostium of smaller arteries and, subsequently, block the flow of blood. Conventional guiding catheters employ perfusion ports that allow increased blood flow through the artery while the catheter is navigated through the arteries. These ports, however, reduce coronary visualization when a contrast medium is injected through the catheter into the artery of a patient.

A pre-operational technique includes injecting a contrast medium into an artery of a patient to determine the location of the narrowed lumen. When a perfusion catheter is employed, some of the contrast dye escapes through the ports; subsequently the amount of contrast dye injected into the patient's target artery is decreased. A decrease in the amount of the contrast medium causes the coronary visualization to decrease. Therefore, when an operator uses a guiding catheter with perfusion ports, the operator compromises the amount of contrast that can be injected into the artery and thereby decreases the visualization of the target artery.

Some prior art devices have been employed to control the efflux of the contrast medium from a catheter. One such device employs two groups of one-way valves. One group of valves prohibits the flow from the arterial lumen to the lumen in the catheter. The other group prevents flow from the catheter lumen to the arterial lumen. Another prior art device uses a one-way check valve inside the main catheter to enable blood to flow through the arterial catheter only when the heart is pumping and prohibit the flow of the contrast from the catheter lumen through the ports.

A need exists for a simple effective device for limiting the loss of contrast dye into the aorta or untargeted arteries while enabling blood flow through an artery in which the guiding catheter is located.

SUMMARY OF THE INVENTION

The present invention discloses a perfusion controlled catheter that allows perfusion of blood through the catheter to the target of the angioplasty procedure via perfusion ports in the catheter body while providing a means to cover the ports during the injection of a contrast medium. This invention eliminates the problems of poor visualization of the target artery associated with perfusion catheters, which results from the loss of dye through the perfusion ports, while still enabling the perfusion of blood to continue as the operator navigates the catheter through the arteries of the patient.

The present invention includes an adjustable member that is disposed in a first position covering the perfusion ports when a contrast is injected through the catheter and is changed to a second position exposing the ports when the catheter is being navigated through the arteries.

In one preferred embodiment, a sleeve or stylet is slidably disposed within the tubular body of a guiding catheter. A guide member connected to the sleeve or stylet rides in a slot in the tubular body of the catheter. The sleeve or stylet is moved by the guide member from a front position blocking the ports to a second position in which the ports in the catheter are uncovered.

In another preferred embodiment, the guiding catheter includes inflatable balloons adjacent to the perfusion ports. A hypotube is imbedded in the walls of the catheter forming an inflation lumen in communication with the inflatable balloons. The hypotube terminates at an injection syringe near the hub of the catheter.

In yet another preferred embodiment, an angioplasty procedure is disclosed in which a guiding catheter is utilized to inject a contrast medium into an artery of a patient prior to angioplasty procedures. Perfusion ports are provided to enable the flow of blood through the guiding catheter. The perfusion ports are covered during the injection of the contrast dye so as to prevent the injection of contrast medium into the aorta or unintended arteries. When the contrast medium is not being injected into the intended artery, the perfusion ports are uncovered to allow the flow of blood through the treated artery.

BRIEF DESCRIPTION OF THE DRAWINGS

FIG. 1 is a diagrammatic view of a prior art guiding catheter;

FIG. 2 is a partial cut-away view of the tube wall of the guiding catheter of FIG. 1;

FIG. 3 is a diagrammatic view of a PTCA procedure using the prior art guiding catheter of FIG. 1;

FIG. 4 is a diagrammatic view of a partial cross-section of the perfusion controlled guiding catheter assembly of the present invention;

FIG. 5A is a frontal view of a stylet shown in the catheter assembly of FIG. 4;

FIG. 5B is a front view of another preferred embodiment of a stylet for use in connection with the catheter assembly of FIG. 4;

FIG. 6 is a cross-sectional view taken along line 6—6 in FIG. 4;

FIG. 7 is a partial cross-sectional view of another guiding catheter assembly in accordance with another preferred embodiment of the present invention;

FIG. 7A is a partial cut-away perspective of a portion of the guiding catheter assembly shown in FIG. 7;

FIG. 8 is a cross-sectional view of the guiding catheter assembly of FIG. 7 taken across line 8—8 in FIG. 7;

FIG. 9 is a partial cross-sectional view of another guiding catheter assembly of another preferred embodiment of the present invention;

FIG. 10 is a cross-sectional view taken along line 10—10 in FIG. 9;

FIG. 10A is a cross-sectional view taken along line 10A—10A in FIG. 10;

FIG. 11 is a cross-sectional view of an alternate preferred embodiment showing a variation on the catheter assembly of FIG. 9 corresponding to the cross-sectional taken along line 10—10 in FIG. 9; and FIG. 11A is a cross-sectional view taken along line 11A—11A of FIG. 11.

DETAILED DESCRIPTION OF THE PREFERRED EMBODIMENT

Referring first to FIG. 1, a typical prior art guiding catheter 10 is shown. The catheter includes a hub section 12 with a luer 13, a strain relief section 14, an extended shaft 16 and a tip 18. The shaft 16 usually includes an outer jacket 20 made of a plastic, such as polyurethane, which provides both support and memory so as to maintain curvature. Beneath the outer jacket is a wire braid 22 which provides torque control and an inner lining 24 made of a low friction materials, such as Teflon, which decreases the friction coefficient between the guide catheter inner wall and the balloon catheter. Guide catheters have certain design differences depending upon whether they are used to access the aorta through the femoral artery (thigh) or brachial artery (upper arm). Thermal plastics may be used in the outer layer 20 in order to enhance the support memory so as to maintain primary curves 26 and secondary curves 28.

As shown in FIG. 2, the walls of the shaft include an outer jacket 20, a inner wire braid lining 22 and a internal hollow core 24 made of a low friction material.

FIG. 3 shows the prior art catheter 10 of FIG. 1 in use in a typical PTCA procedure. In order to access the blood vessels of the heart, the typical PTCA procedure begins with the insertion of guide catheter 10 into the femoral or brachial artery. From there the guide catheter is manipulated into the aorta which terminates at the aortic root 30. The right and left coronary arteries open from the aortic root to provide blood flow passageways for the heart.

As shown in FIG. 3, the tip 18 of catheter 10 is inserted through the aortic root to the opening (ostium) 32 of the right coronary artery (RCA) 34. It is not unusual for the catheter 10 to be of such a size that it effectively blocks all or most of the opening 32 in an artery 34. In order to maintain some essential blood flow through the artery, a plurality of small ports 36, 38 are provided in the shaft 16 of guiding catheter tube 10, usually near the end of the catheter, as shown.

Prior to the insertion of a guide wire and balloon catheter for treating the artery, a contrast medium 40, preferably visualized by x-ray, is injected to determine the location of the blockage. As the contrast medium flows through artery 34, the flow path is traced by an x-ray machine which determines the precise location of the blockage.

During injection, some of the visualization medium is undesirably diffused through perfusion ports 36 and 38, as shown at 42 and 44. This diffusion of medium in the aorta or other arteries which are not of concern can cause serious difficulty in visualizing the blocked artery as well as resulting in an undesirable loss of injection medium where such is not needed. In order to minimize this loss of medium, the perfusion ports 36, 38 are typically made as small as possible, sometimes as small as 1 millimeter in diameter, compared to the diameter of the guiding catheter, typically about 8 French, that is about 0.1". However, such tiny perfusion ports present a problem in not providing openings large enough for the satisfactory flow of blood when the visualization medium is not being injected.

Looking now at FIG. 4, a preferred embodiment of the short exchange guiding catheter assembly 50 according to the present invention is shown. Assembly 50 includes a catheter body 52 and catheter hub 53. Catheter body 52 is formed by a long narrow tube 54, preferably cylindrical in shape, with a outer surface 55 and an inner surface 56. Preferably tube 54 is constructed of a conventional flexible material of the type described above with respect to conventional guiding catheters. Catheter hub 53 is a conventional unit in most respects, similar to hub 12 in FIG. 1.

Exchange catheter tube 54 has a large lumen (passageway) 60 within tubular member body 52 through which a guide wire (not shown) may be slidably disposed, in a conventional manner. Perfusion ports 57, 58 are formed in the wall of catheter tube 54 communicating between large lumen 60 and the exterior of catheter 52. A smaller lumen 64 is formed by an inner passageway 66 in one side of tube 54. The distal end 59 of the passageway 66 terminates below perfusion ports 57, 58. The proximal portion of passageway 66 opens into a slot 69 within catheter wall 54 which communicates with the exterior catheter 52.

A stylet 68 is inserted into passageway 66 and extends the entire length of the passageway to abut the end 59 of the passageway. A remaining portion 67 of stylet 68 extends through slot 69 in the catheter wall 54.

Looking at FIG. 6, the small lumen 64 formed by passageway 66 in the wall of guiding catheter tube 54 is shown. The stylet 68 extends in small lumen 64 to the distal end 59 of passageway 66. The manner in which passageway 66 is formed within the wall 54 of guiding tube 52 is somewhat discretionary. As shown in FIGS. 6 the wall 55 of guiding catheter tube 52 includes a teflon core 24, an inner wire braid jacket 22 and an outer plastic jacket 20, preferably made of urethane. Core 24 is hollow providing for an inner lumen 60 which serves as a guide shaft for the guide catheter assembly 10.

Preferably a portion of the inner core 24 is removed or tapered to form a passageway 66 within which the stylet 68 is disposed. Preferably the wire braid 22 also follows the tapered passageway 66. Outer jacket 20 remains circular in form providing the channel passageway 66 between jacket 20 and wire braid cover 22.

Passageway 66 is preferably formed by removing a portion of inner core 24 from the catheter hub point to the location of the catheter where the balloon 68 is disposed, as shown in FIG. 4. Passageway 66 extends between the wire braid 22 and the outer jacket 20. Alternately, passageway 66 may be formed by providing an irregular shaped inner core 24 (not shown) in which a portion of the circumference is restricted slightly to leave a pocket passageway between that portion and the outer jacket 20.

As shown in FIG. 4, stylet 68 is disposed in passageway 66 so as to block perfusion ports 57, 58. Preferably, stylet 68 is flexible plastic or alloy so that it may be retracted out of opening 69 to the point where the end 70 of stylet 68 is above ports 57, 58 thereby uncovering the ports to enable the normal flow of blood.

In operation, stylet 68 in FIG. 4 is in the closed position when it is advanced in passageway 66 to the point where the end 70 of stylet 68 abuts the end 59 of passageway 66. Stylet 68 is raised to the open position by removing stylet 68 out of passageway 69 until the end of stylet 70 is raised above ports 57, 58.

FIG. 5B shows an alternative stylet 72 which is longer than stylet 68 as shown by end 74. A slot 76 is positioned in stylet 72 to coincide with ports 57, 58 when stylet 72 is in the open position. By pulling stylet 72 upward and out of slot 69, the lower portion 74 blocks ports 57, 58 so that stylet 72 is in the closed position.

Another preferred embodiment is shown in FIG. 7 in which a cylindrical sleeve 80 extends along a passageway 81 within wall 82 of guiding catheter shaft 84. Sleeve 80 terminates above perfusion ports 86, 87 in the inner wall 82 of catheter shaft 84. A tab 88 extends through an opening 89 in catheter wall 84 to connect to sleeve 80 so as to move the sleeve longitudinally within wall 82. The length of opening 89 is sufficient to enable tab 88 to push sleeve 80 downward to cover perfusion ports 86, 87.

As seen in FIG. 7A, inner core 24 has openings 83, 85, having a diameter similar to ports 86, 87 in outer jacket 20 so as to enable flow from internal lumen 78 through holes 83, 85 and perfusion ports 86, 87 to the exterior of the catheter assembly as shown. Referring to FIG. 8, a cross-section of the catheter assembly in FIG. 7 is shown. Sleeve 80 is disposed blocking perfusion port 86. The manner in which sleeve 80 is disposed in passageway 81 may be dictated by the parameters of manufacturing. Preferably, a portion of the inner teflon core 24 is removed as discussed earlier.

Referring now to FIG. 9, another preferred embodiment of the present invention is shown in which a catheter assembly 90 has a hollow catheter tube 92 having a large lumen 93 therein. A small lumen 94 is formed in the wall of catheter tube 92 by hypotube 95 extending from perfusion ports 96, 97 to an inflation syringe 98 exterior of catheter tube 92. Hypotube 95 ends at inflatable balloons 100, 102 disposed immediately behind perfusion ports 96, 97 as shown in FIGS. 10 and 10A.

As seen in FIG. 10, preferably the catheter tube 92 comprises at least an inner core 24 and an outer jacket 20. Preferably passageway 94 is formed by cutting out a portion of inner core 24 or by shaping inner core 24 in an irregular manner as previously discussed.

Referring now to FIG. 11, the operation of the balloon embodiment shown in FIG. 9 is demonstrated. When it is desired to close ports 96, 97, balloons 100, 102 are inflated by the injection of an innocuous solution such as saline from syringe 98 through hypotube 95. As balloons 100, 102 inflate, they extend to cover ports 96, 97, as shown in FIGS. 11 and 11A. The contrast medium is then injected through lumen 93 to the artery to be tested. Ports 96 and 97 are substantially closed to prevent any undesired emission of the contrast medium through those ports. Once the medium has been injected into the artery, the syringe 98 deflates balloons 100, 102 so that the flow of blood again resumes through ports 96, 97.

Preferably, hypotube 95 is a hollow metal tube such as stainless steel and blocking balloons 100, 102 are made out of latex so as to provide strength and flexibility. Syringe 98 is preferably a conventional syringe of a type which can easily inflate and deflate balloons 100, 102 through small lumen 94. The other materials of guiding catheter 92 in accordance with the present invention are normal conventional materials.

A typical outer diameter of catheter tube 92 is approximately 0.104". The conventional inner diameter of a guiding catheter is usually about 0.084". In the present invention, it is expected that the inner diameter of the main lumen is 0.079", leaving a wall thickness of 0.025". The diameter of the small lumen 94 is preferably 0.015". The inflation diameter of securing balloon 86 is preferably at least the size of the perfusion ports so as to securely block the ports when inflated. Similar dimensions are applicable for the other embodiments shown in FIGS. 4–8. In sum, the means to block the ports can be formed by an inflatable device having an inflated diameter at least as great as the diameter of the opening. An inflation means can be used for inflating the inflatable device. The inflatable means can communicate through a passageway in the guide lumen to the inflatable device. The blocking means can also be a tube within the guide lumen of the hollow tubular member, said tube having a second opening therein and being moveable within said lumen between a first position in which the opening and the second opening are aligned and a second position in which the opening and the second opening are not aligned. In each case the blocking means can be referred to as an elongated or elongable member.

Although the foregoing description shows a preferred embodiment of the present invention, it is understood that other obvious modifications or changes may be made within the scope of the present invention. Accordingly, the present invention is intended to encompass such changes and modifications which fall within the intent and scope of the invention.

What is claimed is:

1. A perfusion-controlled guiding catheter for use in angioplasty procedures in an artery to enable the flow of blood between the catheter and the artery while limiting perfusion of contrast medium injected into the catheter, comprising:

(a) a hollow tubular member forming a guide lumen therein through which contrast medium may be injected into the artery, said tubular member having a proximal end, and a distal end adapted for insertion in a patient, and wherein said guide lumen has an aperature at the distal end of the tubular member, (b) an opening in the wall of said tubular member to enable the flow of blood between the guide lumen and the artery, and (c) an elongated member extending substantially the length of the lumen of the tubular member including means for selectively closing the opening, while the lumen remains open, to restrict flow between the lumen and the artery during injection of the contrast medium and for opening the opening to enable flow between the lumen and the catheter.

2. The catheter of claim 1 wherein the opening is formed by a plurality of ports in the wall of the tubular member near the end of the member.

3. The catheter of claim 1 wherein the elongated member is an inflatable device having an inflated diameter at least as great as the diameter of the opening.

4. The catheter of claim 3 and further including inflation means for inflating the inflatable device.

5. The catheter of claim 4 wherein the inflating means communicates through a passageway in the tubular member to the inflatable device.

6. The catheter of claim 1 wherein the elongated member is a tube within the hollow tubular member, said tube having a second opening therein and being moveable within said tubular member between a first position in which the opening and the second opening are aligned and a second position in which the opening and the second opening are not aligned.

7. The catheter of claim 6 wherein the hollow tubular member includes a slot therein and the tube includes a handle extending in said slot.

8. A guiding catheter for use in angioplasty procedures, comprising:
 (a) a guiding catheter hub,
 (b) an elongated guide catheter connected to the guide hub and forming a guide lumen therein for injecting a contrast medium through the guide lumen, said catheter having a proximal end, and a distal end adapted for insertion in a patient, and wherein said guide lumen has an aperature at the distal end of the catheter,
 (c) a port in the guide catheter near the end of the guide catheter for enabling flow between the lumen and external of the guide catheter,
 (d) an elongated member extending substantially the length of the guide catheter and movable within the wall of the guide catheter and having a first position blocking the port while the lumen remains open and a second position not blocking the port, and
 (e) means for selectively changing the positions of the movable member to enable or block flow through the port.

9. The catheter of claim 8 wherein the movable member is an inflatable balloon secured along the wall of the guide catheter near the port.

10. The catheter of claim 8 wherein the movable member is a tube within the guide catheter.

11. In a PTCA procedure, the process of injecting contrast medium through the lumen of a guide catheter having a port and blocking means to selectively block the port therein, comprising the following steps in the sequence set forth:
 (a) introducing the guide catheter within the body of a patient to a point proximate to an artery to be examined,
 (b) moving the blocking means to a position blocking the port,
 (c) injecting the contrast medium through the lumen of the guide catheter to the artery to be examined, and
 (d) moving the blocking means to a position not blocking the port to enable the flow of blood between the guide catheter and the artery.

12. The process of claim 11 wherein moving the blocking means comprises moving a movable elongable member within the guide catheter.

13. The process of claim 11 wherein moving the blocking means comprises moving an inflation balloon having an inflation diameter equal to the diameter of the port.

14. The process of claim 11 wherein moving the blocking means comprises moving a moveable tube within the guide catheter.

* * * * *